United States Patent
Pauletto et al.

(10) Patent No.: US 9,633,173 B2
(45) Date of Patent: Apr. 25, 2017

(54) HANDWRITING RECOGNITION TOOL

(71) Applicant: Quintiles IMS Incorporated, Danbury, CT (US)

(72) Inventors: Stephan Pauletto, Duggingen (CH); Tilman Ebding, Weil am Rhein (DE)

(73) Assignee: Quintiles IMS Incorporated, Danbury, CT (US)

( * ) Notice: Subject to any disclaimer, the term of this patent is extended or adjusted under 35 U.S.C. 154(b) by 146 days.

(21) Appl. No.: 14/202,331

(22) Filed: Mar. 10, 2014

(65) Prior Publication Data
US 2015/0254425 A1 Sep. 10, 2015

(51) Int. Cl.
| | |
|---|---|
| G06F 17/00 | (2006.01) |
| G06F 19/00 | (2011.01) |
| G06K 9/00 | (2006.01) |
| G06Q 50/24 | (2012.01) |
| G06F 17/21 | (2006.01) |
| G06Q 30/02 | (2012.01) |
| G06Q 50/22 | (2012.01) |
| G06F 17/24 | (2006.01) |
| G06Q 10/10 | (2012.01) |

(52) U.S. Cl.
CPC ........ *G06F 19/3456* (2013.01); *G06F 19/328* (2013.01); *G06K 9/00161* (2013.01); *G06K 9/00442* (2013.01); *G06Q 50/24* (2013.01); *G06F 17/211* (2013.01); *G06F 17/24* (2013.01); *G06F 17/242* (2013.01); *G06F 17/246* (2013.01); *G06F 17/60* (2013.01); *G06K 9/00852* (2013.01); *G06Q 10/10* (2013.01); *G06Q 30/02* (2013.01); *G06Q 50/22* (2013.01)

(58) Field of Classification Search
CPC ...... G06F 17/221; G06F 17/24; G06F 17/246; G06F 17/243; G06F 17/60; G06F 19/3456; G06F 19/322; G06F 19/328; G06Q 50/22; G06Q 10/10; G06Q 30/02; G06Q 10/20; G06Q 30/021
USPC .......................... 715/209, 249, 268; 382/119
See application file for complete search history.

(56) References Cited

U.S. PATENT DOCUMENTS

| | | | |
|---|---|---|---|
| 2005/0182656 A1* | 8/2005 | Morey | G06Q 50/22 705/2 |
| 2011/0035662 A1* | 2/2011 | King | G06F 17/211 715/273 |
| 2014/0079297 A1* | 3/2014 | Tadayon | G06K 9/00 382/118 |

* cited by examiner

*Primary Examiner* — Quoc A Tran
(74) *Attorney, Agent, or Firm* — Fish & Richardson P.C.

(57) ABSTRACT

Some implementations may provide a method implemented on a processor, the method includes: receiving, on a computer host, an electronic document representing a pharmaceutical prescription; identifying constituent regions that include at least a first portion and a second portion within the electronic document; identifying first spatial frequencies for the first portion within the electronic document; identifying second spatial frequencies for the second portion within the electronic document; identifying a header based upon the first spatial frequencies; using the header to identify a prescriber; retrieving a profile for the prescriber; analyzing the second spatial frequencies using the profile for the prescriber; and creating, based upon analyzing the second spatial frequencies using the profile for the prescriber, a transaction record on the computer host for a medical transaction associated with the pharmaceutical prescription.

23 Claims, 12 Drawing Sheets

Recognition process

1) Divide the form into vectors.
2) Identify the vectors where forms can be recognized.
3) Apply recognition functions to patterns in vectors.
4) Compare vector function values with vector attribute function values in database.

Recognition sequence

1) Identify the form and the doctor
3) Find vectors for patient, diagnosis, symptoms and pack values.
4) Recognized patterns in the vectors: use reduced dictionary of reference data values.

Learning sequence

1) Read user input for learning
2) Apply recognition functions and store vector and vector attributes per function into database.
3) Re-apply recognition to already stored vector data and re-rack stored entries.
4) Test for former recognition failures using new vector function result.

Sunny Hospital
Senior Care Department

PATIENT: AGE __84__ ans    SEXE  M ☐  F ☒
TAILLE: __1__ M __67__ CM   POIDS: __69__ KG
FUMEUR ☐  ANCIEN FUMEUR ☐    NON FUMEUR ☒

DIAGNOSTICS                Premitre      Reconsultation
                           Consultation
                              ☐              ☒
                              ☐              ☒
                              ☐              ☒

DONNÉES COMPLEMENTAIRES       1    2    3
ENVOI SPECIALISTE pour diagnostic  ☐  ☐  ☐
RETOUR SPECIALISTE pour diagnostic ☐  ☐  ☐

| THERAPIE | DUREE DU TRAITEMENT |
|----------|---------------------|
| Nouv Répété | PREVU (en jours) |

100

Indiquer le dosage et la posologie

EFFETS RECHERCHES:
1. _____
2. _____
3. _____
4. _____
5. _____

Attribute data for cropping

Input filename = RX=02-a.jpg
Left onset position = 81
right onset position = 202
peak no#1 position = 103
peak no#2 position = 192
half width for peak no#1 = 121
half width for peak no#2 = 15

Histogram

Cropped Image

Recognition process

1) Divide the form into vectors.
2) Identify the vectors where forms can be recognized.
3) Apply recognition functions to patterns in vectors.
4) Compare vector function values with vector attribute function values in database.

Recognition sequence

1) Identify the form and the doctor
2) Find vectors for patient, diagnosis, symptoms and pack values.
3) Recognized patterns in the vectors: use reduced dictionary of reference data values.

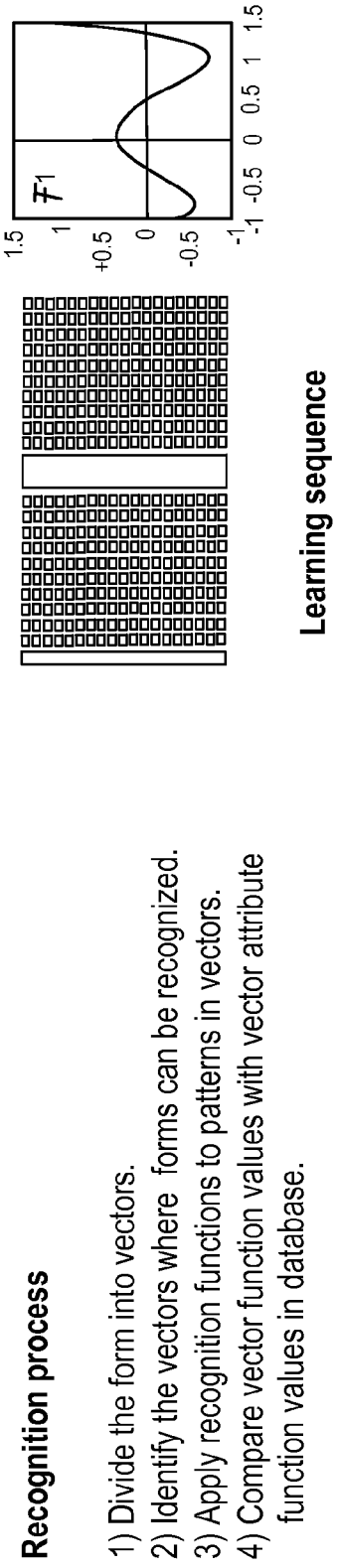

Learning sequence

1) Read user input for learning
2) Apply recognition functions and store vector and vector attributes per function into database.
3) Re-apply recognition to already stored vector data and re-rack stored entries.
4) Test for former recognition failures using new vector function result.

FIG. 7B

HANDWRITING RECOGNITION TOOL

BACKGROUND

Health care remains a complex system to administer with numerous opportunities for error. Given the complexity, administrators may introduce new technologies to improve the quality of health care and reduce costs.

OVERVIEW

In one aspect, some implementations may provide a method implemented on a processor, the method includes: receiving, on a computer host, an electronic document representing a pharmaceutical prescription; identifying constituent regions that include at least a first portion and a second portion within the electronic document; identifying first spatial frequencies for the first portion within the electronic document; identifying second spatial frequencies for the second portion within the electronic document; identifying a header based upon the first spatial frequencies; using the header to identify a prescriber; retrieving a profile for the prescriber; analyzing the second spatial frequencies using the profile for the prescriber; and creating, based upon analyzing the second spatial frequencies using the profile for the prescriber, a transaction record on the computer host for a medical transaction associated with the pharmaceutical prescription.

Implementations may include the following features. Identifying constituent regions may include inspecting an electronic document for a reference object and using the reference object to identify the first and second portions. Identifying the constituent regions may include identifying constituent regions that are delineated independent of content appearing in the electronic document. Identifying the constituent regions may include performing a preliminary degree of processing to identify a document format and using the document format to specify the first and second regions. Identifying the first and second spatial frequencies may include performing a fast Fourier Transform on a portion of a document and translating spatial information into frequency information. Identifying the header based upon the first spatial frequencies may include comparing the first spatial frequencies with a library of frequencies of known headers.

Retrieving the profile for the prescriber may include retrieving a dictionary of terms associated with a practice of the prescriber. Retrieving the profile for the prescriber may include retrieving a dictionary of terms for the prescriber represented in the frequency domain. Retrieving the profile for the prescriber may include retrieving a computer data structure that describes different frequency representations for a term appearing in a dictionary. Retrieving the profile for the prescriber may include retrieving a computer data structure that describes different frequency representations for a term appearing in a dictionary. Retrieving the profile for the prescriber may include retrieving a computer data structure that describes a likelihood of correlation between the second spatial frequencies and different terms appearing in a dictionary.

Creating, based upon analyzing the second spatial frequencies using the profile for the prescriber, the transaction record on the computer host may include creating an electronic document prescription based upon the received electronic document representing the pharmaceutical prescription.

In another aspect, some implementations may provide a computer system, comprising at least one processor, wherein the at least one processor is configured to perform the operations of: receiving, on a computer host, an electronic document representing a pharmaceutical prescription; identifying constituent regions that include at least a first portion and a second portion within the electronic document; identifying first spatial frequencies for the first portion within the electronic document; identifying second spatial frequencies for the second portion within the electronic document; identifying a header based upon the first spatial frequencies; using the header to identify a prescriber; retrieving a profile for the prescriber; analyzing the second spatial frequencies using the profile for the prescriber; and creating, based upon analyzing the second spatial frequencies using the profile for the prescriber, a transaction record on the computer host for a medical transaction associated with the pharmaceutical prescription.

Implementations may include the following features. Identifying constituent regions may include inspecting an electronic document for a reference object and using the reference object to identify the first and second portions. Identifying the constituent regions may include identifying constituent regions that are delineated independent of content appearing in the electronic document. Identifying the constituent regions may include performing a preliminary degree of processing to identify a document format and using the document format to specify the first and second regions. Identifying the first and second spatial frequencies may include performing a fast Fourier Transform on a portion of a document and translating spatial information into frequency information. Identifying the header based upon the first spatial frequencies may include comparing the first spatial frequencies with a library of frequencies of known headers.

Retrieving the profile for the prescriber may include retrieving a dictionary of terms associated with a practice of the prescriber. Retrieving the profile for the prescriber may include retrieving a dictionary of terms for the prescriber represented in the frequency domain. Retrieving the profile for the prescriber may include retrieving a computer data structure that describes different frequency representations for a term appearing in a dictionary. Retrieving the profile for the prescriber may include retrieving a computer data structure that describes different frequency representations for a term appearing in a dictionary. Retrieving the profile for the prescriber may include retrieving a computer data structure that describes a likelihood of correlation between the second spatial frequencies and different terms appearing in a dictionary.

Creating, based upon analyzing the second spatial frequencies using the profile for the prescriber, the transaction record on the computer host may include creating an electronic document prescription based upon the received electronic document representing the pharmaceutical prescription.

In yet another aspect, some implementations provide a computer-readable medium comprising software instructions, that when executed by a computer processor, cause the computer profession to perform the operations of receiving an electronic document representing a pharmaceutical prescription; identifying constituent regions that include at least a first portion and a second portion within the electronic document; identifying first spatial frequencies for the first portion within the electronic document; identifying second spatial frequencies for the second portion within the electronic document; identifying a header based upon the first spatial frequencies; using the header to identify a prescriber; retrieving a profile for the prescriber; analyzing the second spatial frequencies using the profile for the prescriber; and creating, based upon analyzing the second spatial frequencies using the profile for the prescriber, a transaction record on the computer host for a medical transaction associated with the pharmaceutical prescription.

DESCRIPTION OF DRAWINGS

FIG. 1A is an illustration of a prescription that is processed to create a transaction record according to some implementations.

FIG. 7B illustrates how recognition and learning sequences can be combined to increase accuracy and reduce the likelihood of errors.

DETAILED DESCRIPTION

Figure 1B:
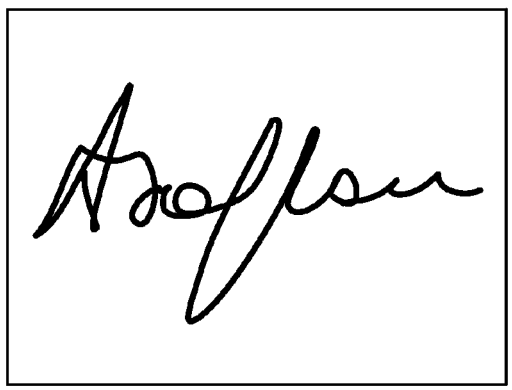
FIG. 1B shows a word pattern taken from one particular prescription form.

Participants in the health care system are seeking to provide greater degrees of accuracy, service, and efficiency through increased use of automation. For example, an insurance company may expedite processing of claims by creating an electronic record that describes a transaction, screening the electronic record for accuracy and other issues, and directing payment where appropriate for claims that can be validated. The insurance company then may analyze systemic results in order to identify dangerous conditions, treatment efficacy, screen for fraud, and provide physician feedback. Other actors in the health care system may attempt to realize other objectives through office automation.

However, different aspects of health care transaction processing may be more difficult to automate and/or possess intrinsic attributes that may make it difficult to incorporate into an automated network. One such area is in the processing of prescriptions. There is a tremendous amount of useful data and desirable systemic objectives that are present in prescription data. For example, pharmaceutical companies may attempt to further determine system efficacy and also determine sales and distribution patterns. Regulatory authorities may attempt to reduce illicit use of controlled substance. Insurance companies may attempt to better manage costs and screen for formulary compliance. Pharmacists may attempt to reduce interpretive errors caused through inaccurate fulfillment of prescriptions. Automated processing of prescriptions may be employed to realize one or more of these objectives. While various degrees of prescriptive electronic prescriptive "pads" or prescribing systems may be employed and/or adopted, the degree of acceptance, automation, and compliance with established procedures may vary with prescriber, facility, and network capabilities (e.g., eScripts or Answers-on-Demand). Even where an electronic prescribing system has been deployed, one or more non-automated hurdles may remain. Thus, a complex and comprehensive system may be required in order to accommodate diverse prescriptive input systems.

In some cases, hard-copies of prescriptions from physician are collected, re-distributed, manually coded on the back-side of the paper and the coded data is manually entered into a computer system. The whole audit may outsourced to an aggregator (e.g., Nielsen) that out-sources operational processes to different companies (e.g., TPC) that operate a number of collocated collection and coding centers where operators attempt to read and process prescriptions. However, the process of employing operators to enter data related to a prescription is time-consuming, error prone and costly. That is, the reading of handwritten prescriptions of arbitrary persons can be very problematic. Handwriting often differs from person to person in size, orientation and many other criteria (e.g., narrowness, width, roundness, angularity and consistency).

The question is whether the content of physician prescriptions may be identified and mapped to reference data (e.g., complying with an IMS Health Reference Data analytic format) by the means of an image processing software application. The operations may be simplified by relating the data set to a specific person related to the writing. This use of author-person specific writing may work better in those circumstances where the same person writes the same words in a similar way. One common example of this principal is how a person executes their signature in a document such as a prescription written to a physician's customized pad. A system may attempt to build an author/person specific dictionary made up of possible and relevant words which can be written into a prescription can be stored in a database that indexed by physician or other health care actor. This person-specific dictionary may include mappings that speak to diagnosis, symptoms, packs, sex and also age.

Thus, an intermediary may process images of handwritten scripts (or aspects of handwriting onto a pad that may be partially printed as a template/standardized form) by breaking down an electronic representation of an image of the script and processing different constituent portions of the electronic representation of the image, at least in part, based on a description of calculated spatial frequencies present within the different constituent portions. For example, an electronic document representing a pharmaceutical prescription may be received on a host. Receiving the electronic document may include receiving a sequence of messages from across an Internet Protocol (IP) network with attached images of prescriptions in messages. The images may be remotely scanned by a pharmacist's office or scanned in bulk at a regional processing center. The host identifies constituent regions that include at least a first portion and a second portion within the electronic document. For example, the first portion may include a header that has been printed onto a pad and the second portion may include a signature block and/or handwritten prescribing data. The host identifies a first pattern of the calculated spatial frequencies for the first portion within the electronic document. For example, the host may perform a Fast Fourier Transform (FFT) of a portion of the script that identifies a physician (or a practice). FFTs may be used to eliminate the impact of image orientation relative to a known structure as information in the frequency domain may be identified in a manner that is not dependent upon precise alignment of the underlying, scanned document. The resident frequencies then may be used as a signature representative of the underlying content.

The host identifies a second pattern of the spatial frequencies for the second portion within the electronic document. Identifying the second pattern of the spatial frequencies may include identifying areas that are associated with the underlying diagnosis, notes, pharmaceutical compound, treatment instructions (dose, times), and other data that is used to convey fulfillment, processing, and/or labeling data required to fulfill a prescription.

The host may identify a header based upon the first pattern of spatial frequencies. The first pattern of spatial frequencies may be deemed to represent a header in that practice information typically appears on some pads in the top (header) portion of a pad. However, the location of the first pattern of spatial frequencies need not be limited to a particular region on a pad. In some cases, the header or first spatial frequencies may be associated with a watermark appearing in miniscule font written into an ornamental delineation around a signature block and/or vertically along a left margin. Identifying a header may include identifying a shorter list of potential practice identifies identified by probabilities.

The host may use the header to identify a prescriber (or practice) and retrieves a profile for the prescriber. For example, the header may identify a particular pediatrician and identify a dictionary listing common terms, diagnoses, prescriptions, warnings, labels, instructions and/or other phrases employed by a prescriber. The host may analyze the second pattern of spatial frequencies using the profile for the prescriber. For example, handwriting recognition may be prone to too many errors when a particular image (or portion of an image) is compared against terms used by a population. However, the likelihood of errors may be reduced when the second pattern of spatial frequencies are limited to a dictionary that has previously been constructed for a prescriber based on the prescriber's prior and current prescribing activity. Based upon analyzing the second pattern of spatial frequencies using the profile for the prescriber, a transaction record on the computer host for a medical transaction associated with the pharmaceutical prescription. For example, a description of a prescription (and the transaction associated with the prescription) may be created in a system that analyzes prescriptions. The prescribing data then may be analyzed for use with insurance and regulatory compliance engines, entered into a claims processing engine, and/or processed by a sales and distribution engine administered for the benefit of a pharmaceutical company.

Multiple techniques may be used to identify a prescriber. For example, a host may look at printed data in association with frequency information present in a user's handwriting. The frequency data may itself be used as a digital signature for use in determining and/or confirming prescriber identity. In some configurations, pattern matching may be applied. Applying the two-dimensional Fast Fourier Transformation alone may not work as well for signatures and other handwriting on forms because of different frequency spaces of form and signature. However, the host may extend the two-dimensional Fast Fourier Transformation by isolating the hand-writing frequency spaces in extra steps.

FIG. 1A is an illustration of a prescription that is processed to create a transaction record based on spatial frequencies within an electronic document. As shown, form 100 illustrates how a printed pad includes printed and handwritten portions that are used by a prescriber to write a prescription. The form 100 includes a printed header (to identify a practice hospital and a subsidiary department), a name of the prescriber (masked in the illustration), a symptom label (masked in the illustration), and a diagnosis label. The form 100 also includes a date of the prescription, and age of the patient, and an indication of the gender (sex) of the patient. Also shown are three prescriptions that indicate a pharmaceutical compound, a dose, and a frequency of consumption.

Figure 1C:
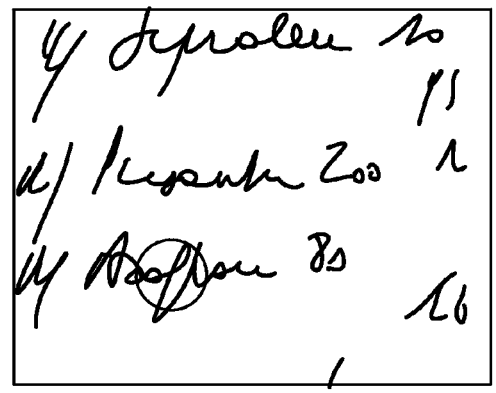
FIG. 1C shows the identified location of the word pattern in the particular prescription form.

FIG. 1B shows a word pattern of "Asaflow" taken from one particular prescription form. For illustration purpose, the word pattern may be present in a number of prescription forms. As demonstrated below, implementations disclosed herein may identify the same word pattern in those prescription forms. FIG. 1C shows a segment of the prescription form where the word pattern was taken from. A circle identifies the location of the word pattern of "Asaflow" in the prescription form. The confidence level is 100%.

Figure 1D:
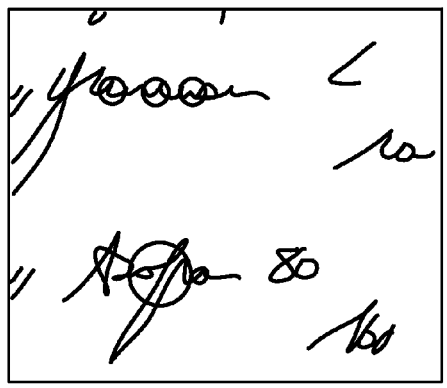
FIGS. 1D to 1G respectively shows the identified location(s) of the word pattern in other prescription forms that include the word pattern.

FIG. 1D shows another prescription form including the word pattern "Asaflow." Four circles, including three small circles and one large circle, correspond to the detected location of the word pattern in the prescription form. The large circle, showing the right location of the word pattern, has a confidence level greater than 80%. The three smaller circles, pointing to the inaccurate location of the word pattern, have confidence levels lower than 50%.

Figure 1E:
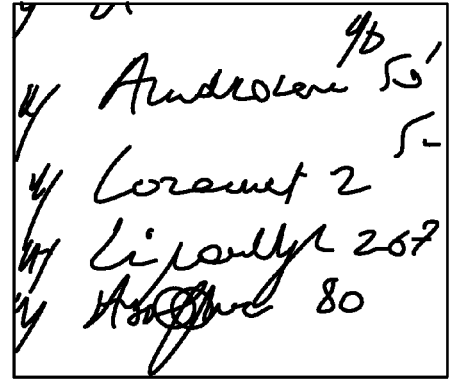

FIG. 1E shows yet another prescription form including the word pattern "Asaflow." Three circles are indicated, each corresponding to the detected location of the word pattern in the prescription form. The upper circle has a confidence level greater than 80%. The upper circle may be detected due to the leading character A. The two lower circles, pointing to about the same location, correspond to the correct location of the word pattern. The two lower circles are large circles and have confidence levels above 50%. Remarkably, the word pattern above the two detected circles appears to have very little disturbing influence on the detectability of the word pattern underneath.

Figure 1F:
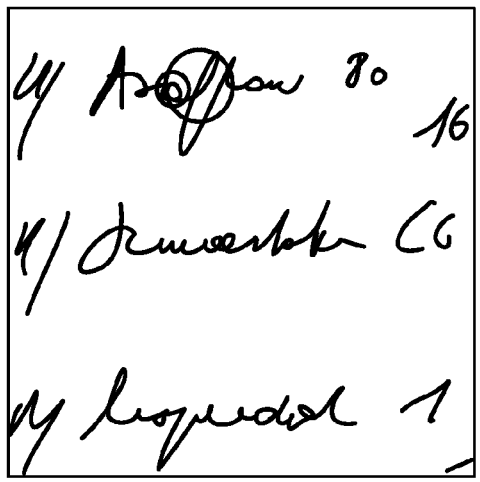

FIG. 1F shows still another prescription form including the word pattern "Asaflow." Two circles are indicated and pointing to substantially the same detected location of the word pattern in the prescription form. The large circle has a confidence level of about 60% and is on the proper position. The small circle has a lower confidence level and is enclosed within the large circle.

Figure 1G:
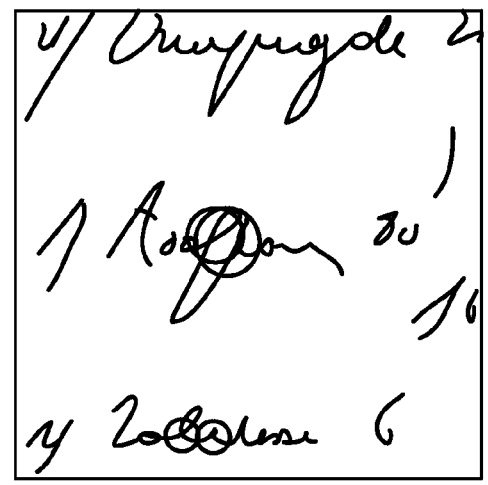

FIG. 1G shows yet still another prescription form including the word pattern "Asaflow." Four circles are shown, in two groups. The first group of two circles point to substantially the same detected location of the word pattern in the prescription form. The large circle has a confidence level of about 60% and is on the proper position. The small circle has a confidence level below 50% and is enclosed within the large circle. The second group of two circles point to another location. However, both circles have confidence levels of under 50%.

Hence, some implementations may identify the locations of a particular word pattern. In these implementations, a threshold comparator may be incorporated to mask locations that are less likely to be to locations of the word pattern.

Figure 2:
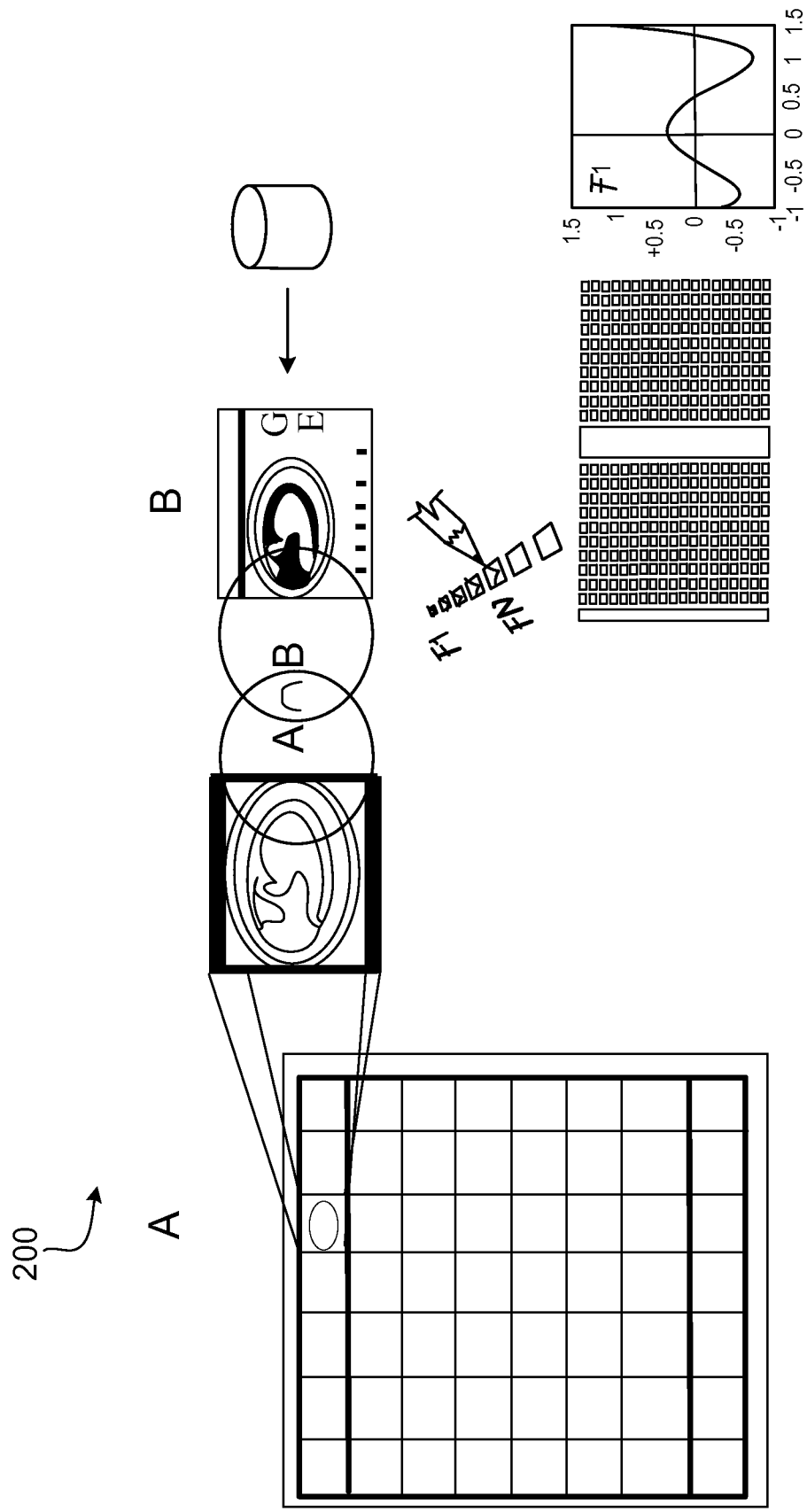
FIG. 2 is an illustration of a configuration illustrating how an electronic document is analyzed.

FIG. 2 is an illustration of a configuration 200 illustrating how an electronic document is analyzed. Configuration 200 illustrates that a pad is broken down into constituent squares so that each square (or region or portion) can be analyzed for frequency information. Note that the orientation of a pad may not always be aligned between identical forms from the same pad. In some cases, the configuration of constituent portions is set based on a uniform marker so that neighbor squares are "set off" from the uniform marker. In other cases, neighboring squares can be analyzed together in order to identify the presence of a common structure in an image that spans multiple squares. The portions (e.g., squares, circles, or other geographic structure) may be overlapping, or the squares may vary in size to minimize the processing that is required to detect an object that is resident in two different portions. Alternatively, or in addition, a drill down analysis may be performed to use a limited number of larger, high level portions that in turn are broken down into smaller areas once the presence of particular objects is identified. Note that each of the portions can be analyzed from a frequency perspective and compared to frequency information for other terms or objects that appear in a global dictionary or a dictionary for a particular profile.

Figure 3:
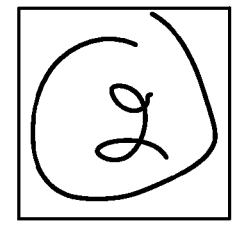
FIG. 3 is an illustration of how a portion of an electronic document can be analyzed.
Figure 3:
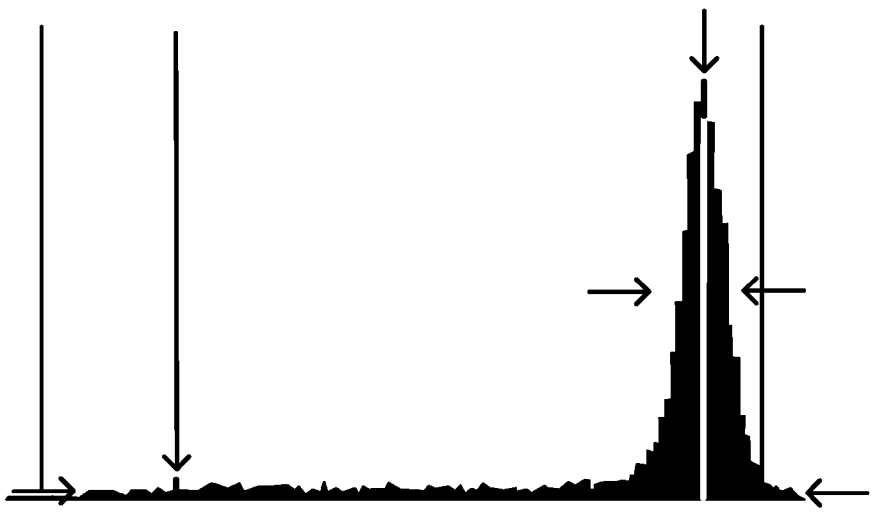

FIG. 3 is an illustration of how a portion of an electronic document is analyzed. In particular, FIG. 3 illustrates a histogram 300 with a description of the contents of the histogram for where the relevant information resides on a frequency perspective. The relative position of this information may be compared with labels for other objects (as could be represented through other histograms) and used to determine the extent to which an object in a scanned image being analyzed relates to a scanned image for a known object.

Figure 4:
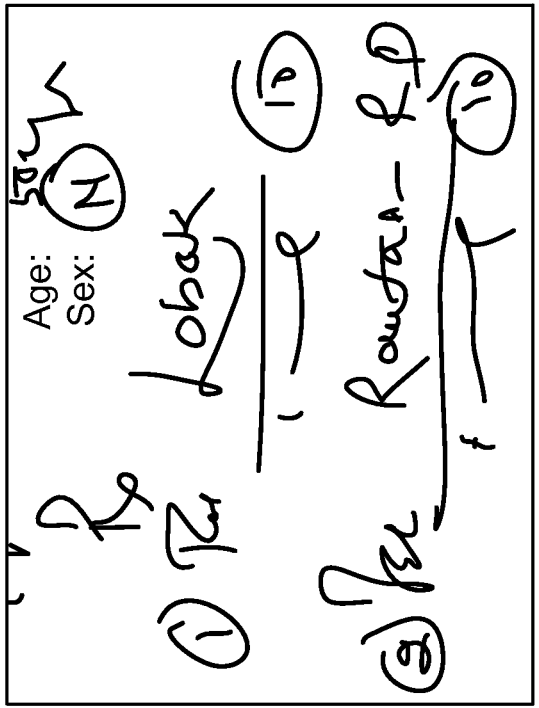
FIG. 4 is an illustration of how a portion of an electronic document can be pre-processed.
Figure 4:
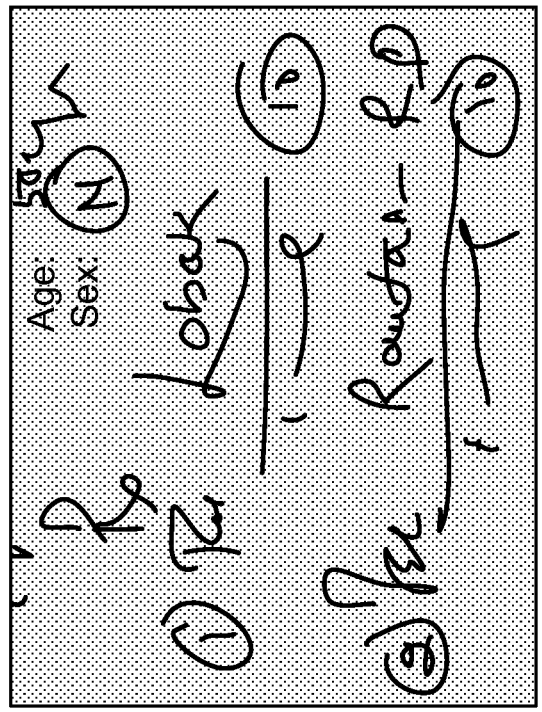

FIG. 4 is an illustration of how a portion of an electronic document undergoes pre-processing. In particular, configuration 400 illustrates how a portion of a constituent portion may be preprocessed before frequency information is compared to remove color artifacts and to strengthen subdued content that reflects, for example, less pressure applied through a pen. As shown, the diminished line widths present in the original image have been reinforced to provide slightly greater dimensions. The greater dimensions may be used to more accurate depict structure that in turn results in more precise description of frequency information. The more precise description of the frequency information may be used to eliminate weaknesses stemming from the inability to properly register spatial frequency components when a particular spatial frequency is present but not accurately detected.

Figure 5:
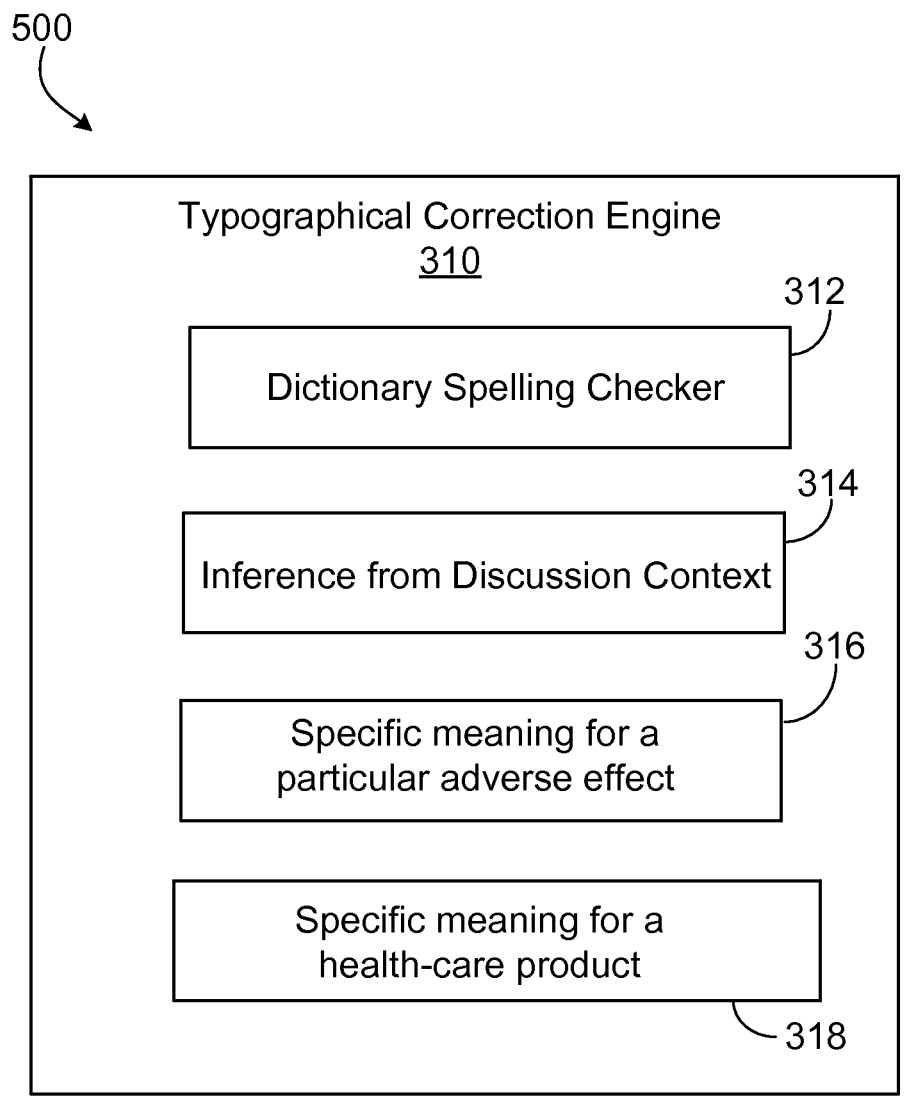
FIG. 5 is an illustration of how an analytical engine on a host may perform autocorrection.

FIG. 5 is an illustration of how an analytical engine on a host performs autocorrection. Specifically, FIG. 5 shows a typographic correction engine 310 for identifying reports of potential adverse effects from consuming a healthcare product according to some implementations. Typographic engine 310 may include dictionary spelling checker 312, an engine for making inference from discussion context 314, an engine for determining specific meaning for an adverse effect 316, and an engine for determining specific meaning for a healthcare product 318. Dictionary spelling checker 312 may include a standard dictionary. In the context of providing typographic correction, the standard dictionary may generally be multi-lingual. The engine for making inference 314 may be configured to correct typos in view of the context. For example, a doctor may wish to enter "rash." Inadvertently, the doctor may have actually entered "trash," even though the doctor meant skin rash. If the prescription is in the context of skin conditions including rashes, then inference checker 314 may correct the word "trash" to "rash." On the other hand, if the patient has registered symptoms of diarrhea, or other digestive issues, then inference checker 314 may not make corrections to the word "trash." Engine for determining specific meaning 316 may correct spellings when a special word exists for describing the particular therapeutic or adverse effect. For example, in the context of a psychology prescription, engine 316 may more likely cause a correction of "happe" as "happy," rather than "happen." Similarly, engine for determining specific meaning for a particular healthcare product may influence the correction of a particular word in view of the particular healthcare product. For example, when the healthcare product being prescribed is an ecstasy pill, engine 318 may more likely cause a correction of "feeling hight" as "feeling high," rather than "feeling right."

Figure 6:
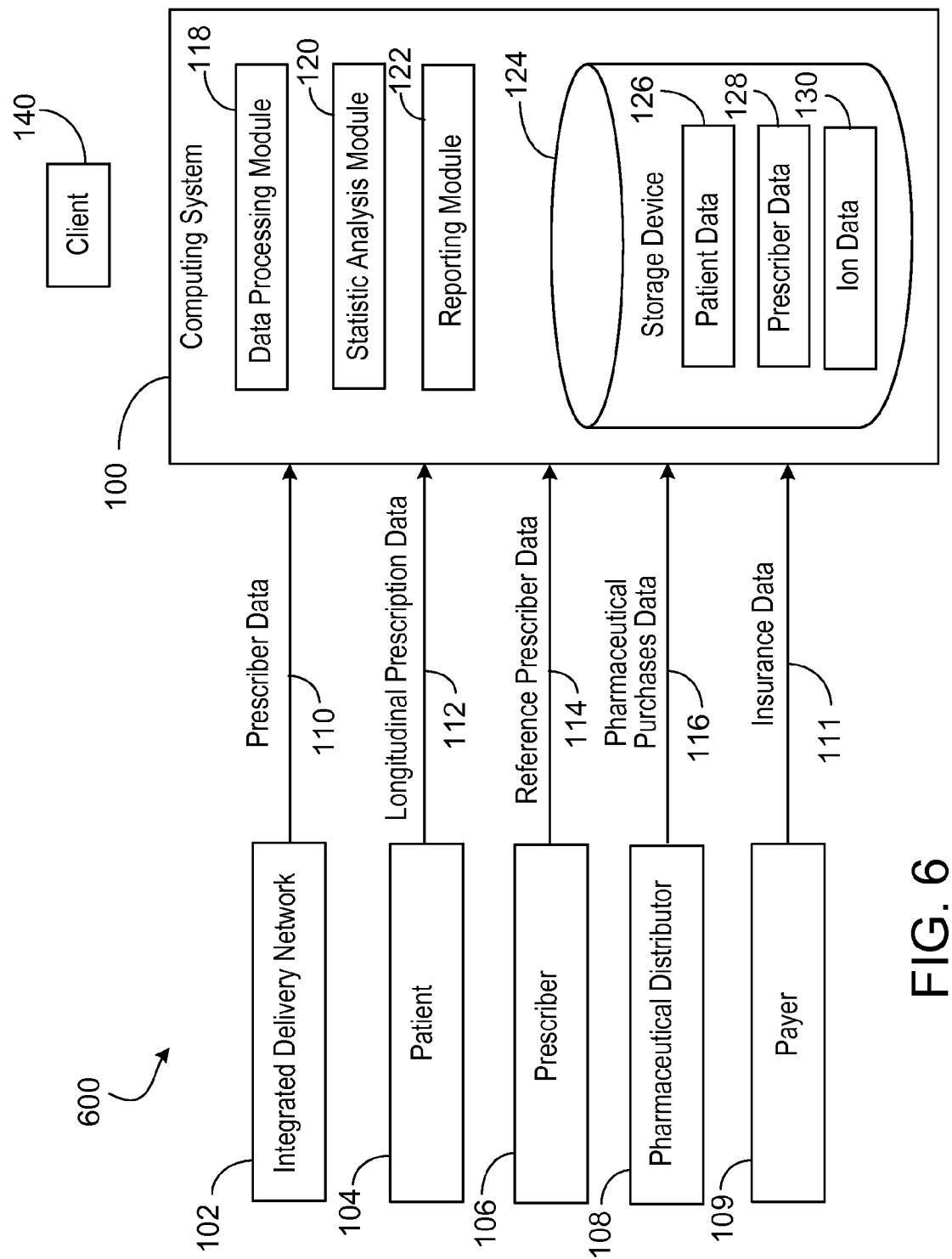
FIG. 6 is an illustration of a system configured to create a transaction record by analyzing spatial frequencies of handwritings within an electronic document.

FIG. 6 illustrates an example analytical infrastructure system implemented in a computing system 100. The computing system may be implemented as a data processing apparatus that is capable of providing the functionality discussed herein, and may include any appropriate combination of processors, memory, and other hardware and software that can receive appropriate medical data and process the data as discussed below. At a high-level, the illustrated example computing system 100 receives various data from sources that are participants in the healthcare process. The sources may include IDNs 102, patient system 104, prescriber system 106, pharmaceutical distributors 108, and payer system 109. The data may include physician prescription data 110, longitudinal patient data 112, reference prescriber data 114, pharmaceutical purchase data 116, and payer's prescription data.

FIG. 6 illustrates the process by which an analytical infrastructure is able to integrate data received about treatment choice, for example, from patient system 104 or from prescriber system 106, with other data sources available in IMS, such as IDNs 102, pharmaceutical distributors 108, and payer system 109. The data from patient system 104 is not restricted to longitudinal patient data 112 but may include any data from a health care provider or the prescriber system 106. The data may include prescription information related to the patient, for example the recent prescriptions written to the patient, and whether or not the prescription drug was covered by the patient's payer or insurance company. It is important to understand that the system may be configured to preserve patient privacy, and will not store nominative data in an aggregated database but only de-identified data. Nominative data for an individual can be compared to the relevant aggregated data, but this may be achieved by using aggregated values in the individual patient application, not by keeping nominative records for multiple patients in a single database. Also, the integration of data from sources other than the user and their medical professionals may be achieved on a de-identified basis except in the instance that the individual gives permission to use their identity information (name, location, gender and age) for the purpose of providing them with their information from another source, such as pharmaceutical purchase data 116 from pharmacies.

The physician prescription data 110 may include data regarding prescriptions prescribed by physicians within an IDN. The prescription data 110 may be received directly from one or more IDNs 102 and represent data reflecting all prescriptions for pharmaceutical products issued by physicians within the one or more IDNs 102, including information about the type of prescription used to obtain the product and the payment method used to purchase the product. As noted previously, this information may be sanitized and aggregated to protect patient privacy. The prescription data may include the total revenue spent on prescriptions based on the specific drug. In some implementations, the data may be based on the total revenue spent on a specific drug in a specific geographic location. The one or more IDNs may provide the retail prescription data 110 on a periodic basis (e.g., every week or month). Though FIG. 6 shows the prescription data 110 being provided directly from the one or more IDNs 102 to the computing system 100, the prescription data 110 may be collected by one or more other intermediate systems and then provided to the computing system 100. If intermediate systems are used, the aggregation and sanitization of the retail prescription data 110 may potentially be performed by the intermediate systems.

The longitudinal patient data 112 may include sanitized retail patient-level data for the one or more patient systems 104. For example, the longitudinal patient data 112 may include information about retail pharmacy-sourced prescription insurance claims, retail pharmaceutical scripts, and/or patient profile data. Longitudinal patient data 112 includes information about aspects of care for the one or more patient systems 104. Though FIG. 6 illustrates the longitudinal patient data 112 as being received by the computing system 100 directly from one or more patient systems 104, the longitudinal patient data 112 may be collected by one or more other systems and then provided to the computing system 100 in a manner analogous to the similar approach discussed for retail prescription data 110. Moreover, the longitudinal patient data 112 may not originate from the one or more patient systems 104, but may rather be provided by one or more prescribers/physicians with whom patient interacts, insurance companies to which a patient submits insurance claims, and/or retailers at which a patient purchases a pharmaceutical product.

The reference prescriber data 114 may include background information for one or more prescribers 106. For example, the reference prescriber data 114 may include a prescriber's demographic information, address, affiliations, authorization data (e.g., DEA, AOA, SLN, and/or NPI numbers), profession, and/or specialty. While most prescribers will be medical doctors, other healthcare professionals such as physician-assistants or nurse practitioners may also be prescriber systems 106. Though FIG. 6 illustrates the reference prescriber data 114 as being received by the computing system 100 directly from one or more prescriber systems 106, the reference prescriber data 114 may be collected by one or more other systems and then provided to the computing system 100 in a manner analogous to the similar approach discussed for retail prescription data 110. Moreover, the reference prescriber data 114 may not originate from the one or more prescriber systems 106, but rather be created and/or maintained by one or more other entities (e.g., government agencies or professional medical organizations) that track information about the prescribing behavior of prescribers 106.

The pharmaceutical purchase data 116 may include information about pharmaceutical purchases made from distributors 108 (e.g., pharmaceutical wholesalers or manufacturers). For example, the pharmaceutical purchase data 116 may include information about the outlet from which a pharmaceutical product is purchased, the type of pharmaceutical product purchased, the location of both the purchaser and seller of the pharmaceutical product, when the purchase was conducted, and/or the amount of a pharmaceutical product that was purchased. Though FIG. 6 illustrates the pharmaceutical purchase data 116 as being received by the computing system 100 directly from one or more distributors 108, the pharmaceutical purchase data 116 may be collected by one or more other systems and then provided to the computing system 100 in a manner analogous to the similar approach discussed for retail prescription data 110. Moreover, the pharmaceutical purchase data 116 may not originate from the one or more distributors 108, but rather be provided by the purchaser of the pharmaceutical product (e.g., a retail outlet).

The insurance data 111 may include information about insurance companies covering the cost of prescriptions. A payer may be the insurance company that covers a patient, or in the case where the patient does not have insurance, and is covered by Medicaid, the payer may be the government. For example, the insurance data 111 may include information about how much of a prescription's cost was covered by the insurance company or by Medicaid. Though FIG. 6 illustrates the insurance data 111 as being received by the computing system 100 directly from one or more payer system 109, the insurance data 111 may be collected by one or more other systems and then provided to the computing system 100.

The various types of data just discussed, which may include prescription data 110, longitudinal prescription data 112, reference prescriber data 114, pharmaceutical purchases data 116, and insurance data 111, are received by computing system 100 in order to derive conclusions based on the data. As noted previously, by the time the data is received by computing system 100, it should have been sanitized so that the data does not include private or confidential information that computing system 100 should not able to access.

For illustrative purposes, computing system 100 will be described as including a data processing module 118, a statistical analysis module 120, a reporting module 122, and a storage device 124. However, the computing system 100 may be any computing platform capable of performing the described functions. The computing system 100 may include one or more servers that may include hardware, software, or a combination of both for performing the described functions. Moreover, the data processing module 118, the statistical analysis module 120, and the reporting module 122 may be implemented together or separately in hardware and/or software. Though the data processing module 118, the statistical analysis module 120, and the reporting module 122 will be described as each carrying out certain functionality, the described functionality of each of these modules may be performed by one or more other modules in conjunction with or in place of the described module.

The data processing module 118 receives and processes one or more of prescription data 110, longitudinal patient data 112, reference prescriber data 114, pharmaceutical purchase data 116, and insurance data 111. In processing the received data, the data processing module 118 may filter and/or mine the prescription data 110, longitudinal patient data 112, reference prescriber data 114, pharmaceutical purchase data 116, and insurance data for specific information. The data processing module 118 may filter and/or mine the received retail prescription data 110, longitudinal patient data 112, reference prescriber data 114, pharmaceutical purchase data 116, and insurance data 111 for specific pharmaceuticals. Thus, any received retail prescription data 110, longitudinal patient data 112, reference prescriber data 114, pharmaceutical purchase data 116, and insurance data 111 that regards pharmaceutical products that are not classified as being associated with a tracked compound or prescription may be disregarded. For example, the received data may be processed by data processing module 118 so as to track use of a specific antibiotic, or of antibiotics in general.

After processing the received prescription data 110, longitudinal patient data 112, reference prescriber data 114, pharmaceutical purchase data 116, and insurance data 111, the data processing module 118 aggregates the processed data into patient data 126, prescriber data 128, and outlet data 130. These groups of data may be stored in storage device 124. In some implementations, the data processing module 118 may create profiles for each patient, prescriber, and the IDN for which data is received.

Prescription data 110 may include prescription information from prescriptions prescribed by a physician within an IDN, information about one or more patients that were prescribed pharmaceutical products, and information about one or more prescribers within the IDN. In this example, data processing module 118 would add information contained in the received prescription data 110 into profiles associated with the IDN, the one or more patients, and the one or more prescribers. In another example, longitudinal patient data 112 may include information about a patient that received prescriptions for a pharmaceutical product and information about one or more prescribers from which the patient received the prescriptions. In this example, data processing module 118 would add information contained in the received longitudinal patient data 112 into profiles associated with the patient and the one or more prescribers.

In other implementations, the data processing module 118 may simply sort and store, in storage device 124, processed prescription data 110, longitudinal patient data 112, reference prescriber data 114, pharmaceutical purchase data 116 and insurance data, the data processing module 118 for later use by other modules.

For each patient system 104, the patient data 126 may include any information related to the prescription and/or sale of one or more types of pharmaceutical products. Patient data 126 may include the quantity of each type of pharmaceutical product the patient has purchased, cumulative days' supply of a pharmaceutical product the patient should still have, cumulative dosage of a pharmaceutical product, medication possession ratio, the number and/or name of doctors from which the patient has received scripts, the number and/or name of retail outlets from which the patient has purchased pharmaceutical products, and/or information regarding the payment method(s) used by the patient when purchasing pharmaceutical products (e.g., cash or insurance).

The prescriber data 128 received from the prescriber system 106, may include any information related to prescriptions written by an identified prescriber for one or more types of pharmaceutical products and the patients to whom the prescriptions were written. Prescriber data 128 may include the quantity of one or more types of pharmaceutical products for which the prescriber has written a prescription, the percentage of prescriptions for one or more types of pharmaceutical products written by a prescriber in relation to the total number prescriptions written by the prescriber, the percentage of prescriptions for one or more types of pharmaceutical products that are paid for with cash, and/or the number of patients for whom the prescriber has written a prescription for one or more types of pharmaceutical products and who currently have a supply of the one or more types of pharmaceutical products that exceeds a threshold. Prescriber data 128 may also include information about which IDN the prescriber is related to if any.

The IDN data 130 may include any information related to prescriptions written to patients for more types of pharmaceutical products, and/or prescribers who wrote the prescriptions. For example, the IDN data 130 may include the quantity of one or more types of pharmaceutical products prescribed by an identified physician within an IDN.

The statistical analysis module 120 uses the patient data 126, prescriber data 128 and/or IDN data 130 to rate and rank individual patients, prescribers, and IDNs. In some implementations, statistical analysis module 120 may compare one or more elements of the patient data 126 corresponding to a patient to averages of the one or more elements of the patient data 126 across a set of patients. Based on the comparison of the one or more elements of the patient data 126, the statistical analysis module 120 may assign one or more ratings to a patient. In other words, for each element of the patient data 126 (e.g., quantity of each type of pharmaceutical product the patient has purchased and percentage of purchases that were made with cash), the statistical analysis module 120 may assign a rating to a patient that reflects how an element of the patient data 126 compares to that same element of other patients in a set with respect to these calculated statistics. Patients in the set used in the comparison may be patients in the same location (e.g., country, state, city, or zip code), patients who share similar patient data (e.g., medical diagnosis or demographic information), and/or patients who share some other relationship.

Similarly, the statistical analysis module 120 may compare one or more elements of the prescriber data 128 corresponding to a prescriber to averages of the one or more elements of the prescriber data 128 across a set of related prescribers. Based on the comparison of the one or more elements of the prescriber data 128, the statistical analysis module 120 may assign one or more ratings to a prescriber. Prescribers in the set used in the comparison may be prescribers in the same location (e.g., country, state, city, or zip code), prescribers who share similar professional data (e.g., practice area or demographic information), and/or prescribers who share some other relationship. The statistical analysis module 120 may be able to derive conclusions for prescribers from the prescriber data 128, in a manner similar to that used for the patient data. For example, it may determine that general practitioners in one county tend to prescribe generic drugs with patients with epilepsy, while neurologists are more likely to use branded drugs for their patients with a similar diagnosis. These determinations may, for example, be used to suggest that a pharmaceutical company should promote a new anticonvulsant more heavily to neurologists than to general practitioners.

The statistical analysis module 120 may also compare one or more elements of the IDN data 130 corresponding to an IDN to averages of the one or more elements of the IDN data 130 across a set of related IDN outlets. Based on the comparison of the one or more elements of the IDN data 130, the statistical analysis module 120 may assign one or more ratings to an IDN. Retail outlets in the set used in the comparison may be retail outlets in the same location (e.g., country, state, city, or zip code), prescribers who share similar commercial data (e.g., size of the retail outlet), and/or prescribers who share some other relationship. For example, the data may indicate that certain drugs are more often bought at rural pharmacies, and other drugs are bought at urban pharmacies. For example, these determinations may suggest that pharmacies should stock more antihistamines for pollen allergies at their rural branches.

The ratings assigned to a patient, prescriber, and/or retail outlet by the statistical analysis module 120 may be normalized numbers that reflect the analysis performed with regard to an element of the patient data 126, prescriber data 128 and/or outlet data 130. In some implementations, the ratings determined by the statistical analysis module 120 may be updated on a periodic basis (e.g., weekly or monthly) or updated any time new data regarding the element corresponding to the rating is received by the computer system 100. Alternatively, in some implementations, the ratings determined by the statistical analysis module 120 may be calculated every time the statistical analysis module 120 receives a query for the ratings.

The statistical analysis module 120 may also calculate a composite rating for each patient, prescriber, and/or retail outlet for which data has been received by the computer system 100. In some implementations, the statistical analysis module 120 may weight each of the individual element ratings associated with a patient, prescriber, or retail outlet and apply an equation to calculate a composite of the individual element ratings. Alternatively, in some implementations, the statistical analysis module 120 may select a proper subset of the available individual element ratings and calculate a composite rating based on the selected individual element ratings.

In some implementations, the statistical analysis module 120 may calculate other metrics. For example, that statistical analysis module may calculate the potential decrease in market size with a change in payer structure. For example, the statistical analysis module may calculate that there may be a limit in market size by 75% if, for a specific geographical area, where most of the residence are supported under a tier three coverage program (that is designed to cater to low income residence) if there were to be an introduction of a tier one coverage plan.

In some implementations, the statistical analysis module 120 may rank patient, prescriber, and/or retail outlet with respect to one another based on the determined ratings. For example, the statistical analysis module 120 may rank all of the patients in a given location (e.g., a zip code) based on each patient's composite rating. Such an approach allows consideration of patient information for a population in a specific location, which is helpful because the patient behavior of interest may be for a localized population. In another example, the statistical analysis module 120 may rank all of the prescribers who are oncologists in a given state based on each prescriber rating related to the quantity of one or more types of pharmaceutical products for which the prescriber has written a prescription (i.e., an element of the prescriber data 128). Such an approach may be useful because specialists may prescribe differently than generalists and it may be of interest to compare the care strategies used by these different groups of prescribers, as discussed above.

In some implementations, the statistical analysis module 120 may use the data collected to generate a modeled rule for an IDN identified as having a market presence. In these implementations, the system may access the historical prescription data, longitudinal prescription data, prescriber data, pharmaceutical purchase data and insurance data to identify the presence of an influence of an IDN. The data uses the demographic information to determine the geographical area influenced by the IDN. For example, prescriber data may include an identifier that is used to identify the IDN the prescriber is affiliated with, if any. The insurance data may also be used to identify the market presence of one or more IDNs. The statistical analysis module 120 may use the data for a specified geographical area to determine the change in market size for a particular product due to the presence of one or more IDNs or a government program within the area. In these implementations, the system may use data from other geographical areas that may not be influenced by the same IDNs or government programs to calculate a market share for a product and project the calculated market share value for the geographical area in analysis. For example, the statistical module may predict a market share for a product in a geographic area to be decreased by 45 percent due the influence of one or more IDNs or government programs. The IDNs or government program in the above example may not support the product patients treated within the network and therefore cause an overall decrease in the market presence of the product.

In these implementations, the statistical analysis module 120 may use the generated modeled rule to predict the prescribing patterns of one or more physicians affiliated to an IDN that has been identified as having a market presence. For example, the statistical ranking module may access prescriber data obtained over the first quarters of a year to predict prescribing patterns of a physician for the second and third quarters of the year. In another example, the statistical analysis module may be able to predict the number of prescriptions prescribed by a prescriber for the upcoming month based on the modeled rule. The prescriber data may include the number of prescriptions written for a particular product each month, the number of repeated prescriptions that the prescriber wrote, i.e. the same prescription for the same patient. The data may also include the details with respect to the prescriber's behavior related to which product was prescribed for treating a specific ailment. For example, the data may include that a prescriber prescribed Lipitor to 95 patients suffering from high cholesterol, but prescribed Crestor for 30 of the patients with the same medical condition.

The reporting module 122 prepares reports based on the ratings and/or rankings calculated by the statistical analysis module 120. The reports prepared by the reporting module 122 may include one or more of the ratings calculated by the statistical analysis module 120 as well as any other data contained in the patient data 126, prescriber data 128 and/or outlet data 130. For example, a report generated by the reporting system may include composite ratings for all prescribers in a given state for a particular pharmaceutical product (e.g., oxycodone—a controlled substance).

The system shown may be filtered and/or mined based on any one or more criteria associated with a patient, prescriber, and/or retail outlet. The reports may be filtered and/or mined based on location, type pharmaceutical product, medical specialty of a prescriber, category of a retail outlet (e.g., large chain retail outlet), and or one or more ratings calculated by the statistical analysis module 120. In other words, any data received and processed by the data processing module 118 or any ratings or rankings calculated by the statistical analysis module 120 may be included in or used to filter and/or mine the data included in a report.

Additionally, in some implementations, the reports generated may be either dynamic or static. The reporting module 122 may generate a report that includes data presented in one or more static formats (e.g., a chart, a graph, or a table) without providing any mechanism for altering the format and/or manipulating the data presented in the report. In such an implementation, the data presentation is generated and saved without incorporating functionality to update the data presentation. In some implementations, the reporting module 122 provides a static report in a PDF, spreadsheet, or XML format. Such a format generally provides an understanding of the reporting module 122 as textual data or a visualization, but other forms of presenting conclusions such as audio, video, or an animation are not excluded as potential results from reporting module 122.

Additionally or alternatively, the reporting module 122 may generate a report that includes controls allowing a user to alter and/or manipulate the report itself interactively. For example, the reporting system may provide a dynamic report in the form of an HTML document that itself includes controls for filtering, manipulating, and/or ordering the data displayed in the report. Moreover, a dynamic report may include the capability of switching between numerous visual representations of the information included in the dynamic report. In some implementations, a dynamic report may provide direct access as selected by a user to some or all of the patient data 126, prescriber data 128 and/or outlet data 130 prepared by the data processing module 118 and/or the statistical analysis module 120, as opposed to allowing access to only data and/or ratings included in the report itself.

One or more clients 140 may interface with the computing system 100 to request and receive reports created by the reporting system. In some implementations, the one or more clients 140 may include a web browser that provides Internet-based access to the computing system 100. Through the web browser, a user of a client 140 (e.g., a wholesaler, a retail outlet, or a prescriber) may request a static or dynamic report from the reporting system as discussed above.

There may be any number of clients 140 associated with, or external to, the example computing system 100. While the illustrated example computing system 100 is shown in communication with one client 140, alternative implementations of the example computing system 100 may communicate with any number of clients 140 suitable to the purposes of the example computing system 100. Further, the term "client" and "user" may be used interchangeably as appropriate without departing from the scope of this disclosure. Moreover, while the client 140 is described in terms of being used by a single user, this disclosure contemplates that many users may share the use of one computer, or that one user may use multiple computers.

The illustrated client 140 is intended to encompass computing devices such as a desktop computer, laptop/notebook computer, wireless data port, smartphone, personal digital assistant (PDA), tablet computing device, one or more processors within these devices, or any other suitable processing device. For example, the client 140 may include a computer that includes an input device, such as a keypad, touch screen, or other device that can accept user information, and an output device that conveys information associated with the operation of the computing system 100. The input device may be used by client 140 to provide instructions to computing system 100 that computing system 100 can execute to provide information requested by client 140 from the various data that computing system 100 receives.

In some implementations, functionality described as being performed by the computing system 100 may be performed by the client 140. For example, the computing system 100 may provide a client 140 with direct access to the ratings and rankings calculated by the statistical analysis module 120. As a result, some or all of the functionality described as being performed by the reporting module 122 may be performed locally by the client 140. The analytical infrastructure may be supported on a webpage application that a client may use to view the data received by the computing system at the analytic infrastructure.

Figure 7A:
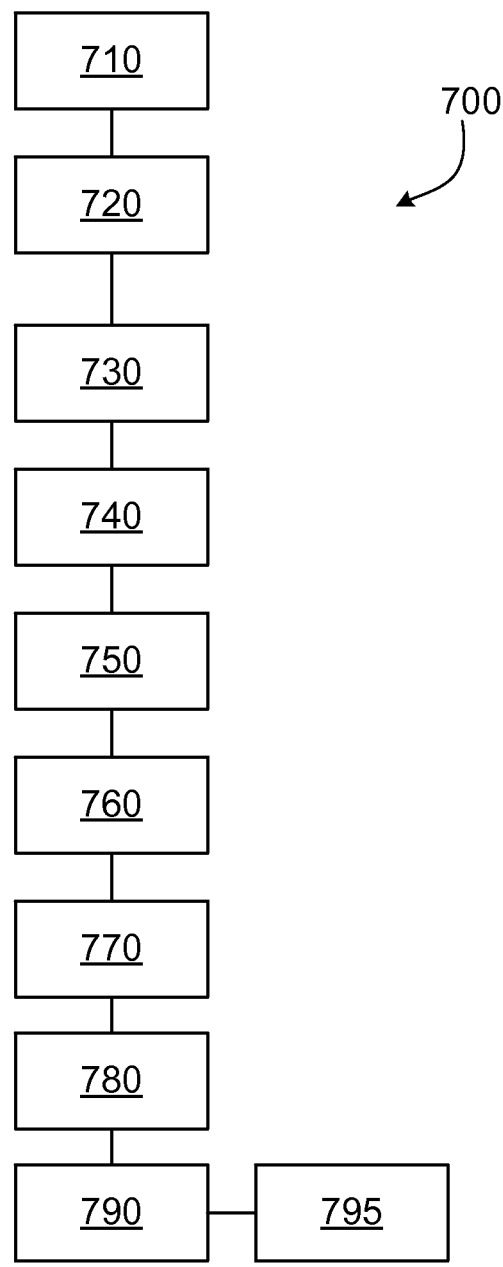
FIGS. 7A and 8 are examples of processes by which a system is configured to create a transaction record by analyzing spatial frequencies of handwritings within an electronic document.

FIG. 7A is a flow chart 700 of a process by which handwriting in a prescription may be analyzed in order to create a transaction record for a medical transaction associated with a pharmaceutical prescription. Generally, the operations described in FIG. 7A may be performed using the user interfaces, configurations, and systems described previously.

A host receives an electronic document representing a pharmaceutical prescription (710). For example, a pharmacist's office may scan in a prescription for processing, approval, and payment. Alternatively, a regional scanning facility may perform batch processing using a high volume scanner.

The host identifies constituent regions that include at least a first portion and a second portion within the electronic document (720). For example, the host may identify prescriber information that has been preprinted (or handwritten) and data for the underlying prescription itself.

The host identifies a first pattern of spatial frequencies for the first portions within the electronic document (730). For example, the host may perform a FFT on a file representing the image from the first portion. The host also identifies a second pattern of spatial frequencies for the second portion within the electronic document (740). The second portion may include an indication of the underlying pharmaceutical compound (or therapeutic treatment regimen), a dosage, and a frequency.

The host identifies a header based upon the first spatial frequencies (760). The header may include prescriber information and represent data that was entered using a printer, for example, as the pad was fabricated and may include the use of a watermark designed to combat fraud. The host may use the header to identify a prescriber (770). Identifying a prescriber may include identifying an indication of an identity that is used to associate handwritten and prescribing behavior that differs with other identities. The host retrieves a profile for the prescriber (780). For example, the profile may include an indication of which pharmaceutical compounds are typically prescribed, the dosage, and frequency. Note that the profile also may include a fine degree of precision that describes prescribing behavior based upon the characteristics of the patient. A profile may describe or favor common pediatric treatment regiments for pediatric patients. The host analyzes the second spatial frequencies using the profile for the prescriber (790). The host may determine that the second portion includes a treatment for a specific infection at a specified dosage based on a profile that includes a vocabulary and terms supporting a physician that treats infection diseases.

The hosts creates, based upon analyzing the second spatial frequencies using the profile for the prescriber, a transaction record for a medical transaction associated with the pharmaceutical prescription (795). The medical transaction record may represent a post-delivery record that is used for analysis or may represent a pre-approved record for consideration and further vetting.

The host may be configured to dynamically respond to emerging trends, fault conditions, or failure-to-resolve rates based on attempts to incorporate transactions into a transaction resolution and analytical system method (not shown). The host may be configured to first recognize a form in order to map potential authors/prescribers to a limited number of prescribers. The host also may be configured to recognize a signature in order to confirm author identity. Major vectors where relevant text is found may be recognized. For example, some pads are printed to foster and encourage entry of certain data into certain areas. A first pad format may encourage the entry of certain data in certain areas. Disease diagnosis may be entered into a first region as labeled on a form while an indication of a particular pharmaceutical compound may be encouraged in a second area, dosage in a third area, frequency in a fourth area, and special warnings and contraindications represented in a fifth area. The pad may be configured to separation of form (printed) and handwritten text to delineate different regions and to facilitate the use of different frequencies in different areas.

Printed text appearing in the form itself may undergo optical character recognition in order to better and more definitively resolve certain aspects (e.g., prescriber identity).

The host may be configured to recognize where specified words or areas where characters are found, for example, based on known conventions and/or known conventions for a particular pad or practice. The host may be configured to recognize characters and its mapping to parts of words. For example, if the prescription is for an oncologist, the dictionary may be configured to increase the likelihood that anti-nausea measures are recognized in the handwritten portion of a pad. The host may be configured to compensate based on samples read. If the host resolves to a certain condition erroneously and the system receives error reports, either through cross-correlation with a claims processing engine or through administrator review or sample of results, the error reports may be used to deemphasize the identification of results associated with the problematic condition. Multiple aspects and sequences may be combined to allow for documents to be quickly processed in a reliable manner that reduces the need for human interventions. FIG. 7B illustrates how recognition and learning sequences can be combined to increase accuracy and reduce the likelihood of errors.

Figure 8:
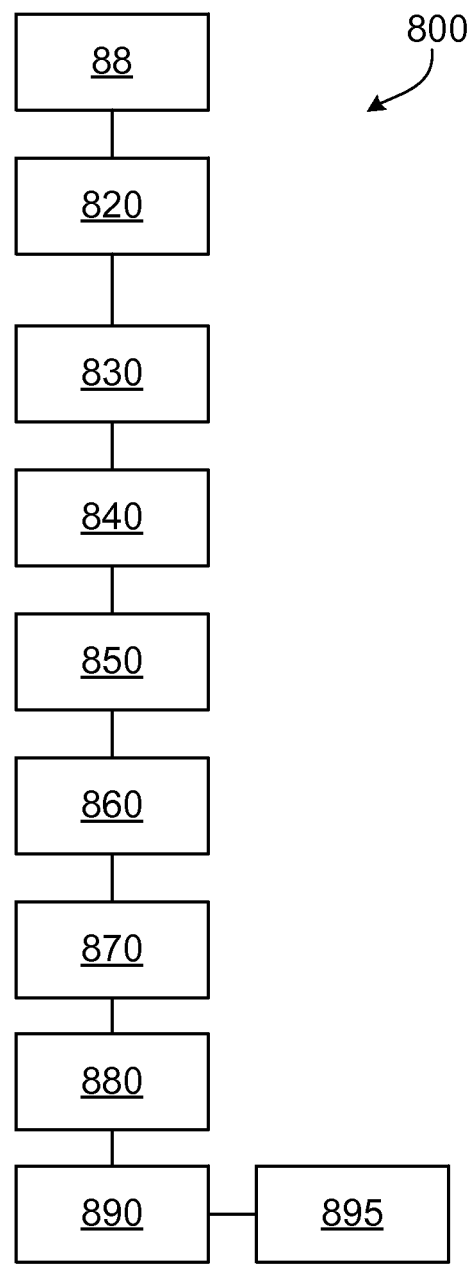

FIG. 8 is a flow chart of a process 800 by which a medical record is created to support a pediatric patient being treated for an infectious disease (e.g., a staph infection). A host receives an electronic document representing a pharmaceutical prescription for an antibiotic that has been scanned in by a pharmacist's office using a local scanner and sent across an IP network using a secure, encrypted protocol (810). The host identifies constituent regions that include at least a first portion in the top of the received image where headers would expected to be found and a second portion within the electronic document wherein the underlying prescription data would typically be located (820). The host may perform a FFT to identify first spatial frequencies for the header (830). The host identifies second spatial frequencies for the actual prescription appearing within the electronic document (840). A header with physician information is identified based upon the first spatial frequencies (850). The host uses the header to identify a prescriber (860) and the host retrieves a profile for the prescriber (870). The host analyzes the second spatial frequencies using the profile for the prescriber (880). For example, the host may load a table of frequencies representing the most common terms and treatments associated with the prescriber (890). The host creates, based upon analyzing the second spatial frequencies using the profile for the prescriber, preauthorization record on the computer host for a medical transaction associated with the pharmaceutical prescription (895). A payor (e.g., an insurance company) then may selectively approve the proposed transaction.

In some configurations, actual handwriting recognition is not performed. Rather, individual word (connected characters) of the prescription has to be taken as a pattern and the result of recognition is the result of mapping a pattern that has to be recognized to the most similar pattern stored in a database. In still other configurations, a portion of handwriting recognition is performed to better identify a particular prescriber or identify a portion of which dictionary should be used within a larger dictionary for a prescriber.

Note that while the operations may be described with respect to a two dimensional Fourier Transform converts a representation of a digital image from the spatial domain into the frequency domain, other transformations may be used. The transformation is used to correlate an unknown image with a known pattern (i.e., a doctor's signature). In the frequency domain, the correlation procedure may be simpler and faster than in the spatial domain. The multiplication of both transformations (image and pattern) and the following inverse transformation may directly reveal the position(s) of 100% accuracy, sufficiently good correlations, bad/weak correlations, or no correlation in the original image.

The host may implement additional geometric methods to enhance the accuracy of results that are identified. These geometric methods may include, but are not limited to:

Line detection
Detection of lines
Determination of coving
Determination of line length
Determination of line crossing In addition to the operations described above, the host may be configured to develop or use pieces of software that can be used to (1) recognize the doctor who has written the prescription, (2) recognize age and sex of the patient, (3) recognize symptoms and diagnosis, (4) recognize the pack name on the prescription, (5) recognize the pack quantity on the prescription. Conformance with established or expected protocols also may be performed.

The system may be configured to identify a document, encrypt the document, and compress the results. Each image may receive a unique identifier, a compression identifier, and security encrypted RX-scan. Scanned documents may be identified with a unique identifier for consistent data processing. For safe and cost efficient storage, the electronic document may be compressed and encrypted.

A received image may be compared with sample set to map a document to a distinct physician. Form patterns may be removed, gaps may be removed from a form, and text overlaps may be refilled. Form sections and handwriting patterns are read from dictionary. These additional preprocessing operations may be used to reduce processing time and enable later updates to a particular dictionary of handwriting patterns.

3.1 Determination of interrelated empty spaces
3.2 Division of remaining spaces
4. Methods for the recognition of continuous lettering Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a Graphic Processing Unit (GPU), a FPGA (field programmable gate array), or an ASIC (application specific integrated circuit). In one example, a CUDA-based GPU may be used. In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a GPU, a FPGA (field programmable gate array), or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media (transitory or non-transitory, as appropriate) suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

What is claimed is:

1. A method implemented on a processor, the method comprising:
   receiving, on a computer host, an electronic document representing a pharmaceutical prescription;
   identifying constituent regions that include at least a first portion and a second portion within the electronic document;
   identifying first spatial frequencies for the first portion within the electronic document;
   identifying second spatial frequencies for the second portion within the electronic document;
   identifying a header based upon the first spatial frequencies, wherein identifying the first and second spatial frequencies includes performing a fast Fourier Transform on a portion of a document and translating spatial information into frequency information such that (i) the header identifying the prescriber is identified from the first spatial frequencies; and (ii) the second spatial frequencies are analyzed using the profile of the identified prescriber;
   using the header to identify a prescriber;
   retrieving a profile specific for the prescriber;
   analyzing the second spatial frequencies using the profile specific for the prescriber such that the second spatial frequencies are compared to spatial frequency domain information from the profile specific for the prescriber, the prescriber-specific profile constructed from the prescriber's past records and including isolated handwriting of the prescriber in a spatial frequency domain; and
   creating, based upon results from analyzing the second spatial frequencies using the profile for the prescriber, a transaction record on the computer host for a medical transaction associated with the pharmaceutical prescription.

2. The method of claim 1, wherein identifying constituent regions includes inspecting an electronic document for a reference object and using the reference object to identify the first and second portions.

3. The method of claim 1, wherein identifying the constituent regions includes identifying constituent regions that are delineated independent of content appearing in the electronic document.

4. The method of claim 1, wherein identifying the constituent regions includes performing a preliminary degree of processing to identify a document format and using the document format to specify the first and second regions.

5. The method of claim 1, wherein identifying the header based upon the first spatial frequencies includes comparing the first spatial frequencies with a library of spatial frequencies of known headers.

6. The method of claim 1, wherein retrieving the profile for the prescriber includes retrieving a dictionary of terms associated with a practice of the prescriber.

7. The method of claim 1, wherein retrieving the profile for the prescriber includes retrieving a dictionary of terms for the prescriber represented in the spatial frequency domain.

8. The method of claim 1, wherein retrieving the profile for the prescriber includes retrieving a computer data structure that describes different spatial frequency representations for a term appearing in a dictionary.

9. The method of claim 1, wherein retrieving the profile for the prescriber includes retrieving a computer data structure that describes different spatial frequency representations for a term appearing in a dictionary.

10. The method of claim 1, wherein retrieving the profile for the prescriber includes retrieving a computer data structure that describes a likelihood of correlation between the second spatial frequencies and different terms appearing in a dictionary.

11. The method of claim 1, wherein creating, based upon results from analyzing the second spatial frequencies using the profile for the prescriber, the transaction record on the computer host includes creating an electronic document prescription based upon the received electronic document representing the pharmaceutical prescription.

12. A computer system, comprising at least one processor, wherein the at least one processor is configured to perform the operations of:
   receiving, on a computer host, an electronic document representing a pharmaceutical prescription;
   identifying constituent regions that include at least a first portion and a second portion within the electronic document;
   identifying first spatial frequencies for the first portion within the electronic document;

identifying second spatial frequencies for the second portion within the electronic document;

identifying a header based upon the first spatial frequencies, wherein identifying the first and second spatial frequencies includes performing a fast Fourier Transform on a portion of a document and translating spatial information into frequency information such that (i) the header identifying the prescriber is identified from the first spatial frequencies; and (ii) the second spatial frequencies are analyzed using the profile of the identified prescriber;

using the header to identify a prescriber;

retrieving a profile specific for the prescriber;

analyzing the second spatial frequencies using the profile specific for the prescriber such that the second spatial frequencies are compared to spatial frequency domain information from the profile specific for the prescriber, the prescriber-specific profile constructed from the prescriber's past records and including isolated handwriting of the prescriber in a spatial frequency domain; and creating, based upon results from analyzing the second spatial frequencies using the profile for the prescriber, a transaction record on the computer host for a medical transaction associated with the pharmaceutical prescription.

13. The computer system of claim 12, wherein the operation of identifying constituent regions includes inspecting an electronic document for a reference object and using the reference object to identify the first and second portions.

14. The computer system of claim 12, wherein the operation of identifying the constituent regions includes identifying constituent regions that are delineated independent of content appearing in the electronic document.

15. The computer system of claim 12, wherein the operation of identifying the constituent regions includes performing a preliminary degree of processing to identify a document format and using the document format to specify the first and second regions.

16. The computer system of claim 12, wherein the operation of identifying the header based upon the first spatial frequencies includes comparing the first spatial frequencies with a library of spatial frequencies of known headers.

17. The computer system of claim 12, wherein the operation of retrieving the profile for the prescriber includes retrieving a dictionary of terms associated with a practice of the prescriber.

18. The computer system of claim 12, wherein the operation of retrieving the profile for the prescriber includes retrieving a dictionary of terms for the prescriber represented in the spatial frequency domain.

19. The computer system of claim 12, wherein the operation of retrieving the profile for the prescriber includes retrieving a computer data structure that describes different spatial frequency representations for a term appearing in a dictionary.

20. The computer system of claim 12, wherein the operation of retrieving the profile for the prescriber includes retrieving a computer data structure that describes different spatial frequency representations for a term appearing in a dictionary.

21. The computer system of claim 12, wherein the operation of retrieving the profile for the prescriber includes retrieving a computer data structure that describes a likelihood of correlation between the second spatial frequencies and different terms appearing in a dictionary.

22. The computer system of claim 12, wherein the at least one processor is further configured to perform the operations of creating, based upon results from analyzing the second spatial frequencies using the profile for the prescriber, the transaction record on the computer host includes creating an electronic document prescription based upon the received electronic document representing the pharmaceutical prescription.

23. A computer-readable medium comprising software instructions that, when executed by a computer, causes the computer to perform the operations of:

receiving, on a computer host, an electronic document representing a pharmaceutical prescription;

identifying constituent regions that include at least a first portion and a second portion within the electronic document;

identifying first spatial frequencies for the first portion within the electronic document;

identifying second spatial frequencies for the second portion within the electronic document;

identifying a header based upon the first spatial frequencies, wherein identifying the first and second spatial frequencies includes performing a fast Fourier Transform on a portion of a document and translating spatial information into frequency information such that (i) the header identifying the prescriber is identified from the first spatial frequencies; and (ii) the second spatial frequencies are analyzed using the profile of the identified prescriber;

using the header to identify a prescriber;

retrieving a profile specific for the prescriber;

analyzing the second spatial frequencies using the profile specific for the prescriber such that the second spatial frequencies are compared to spatial frequency domain information from the profile specific for the prescriber, the prescriber-specific profile constructed from the prescriber's past records and including isolated handwriting of the prescriber in a spatial frequency domain; and creating, based upon results from analyzing the second spatial frequencies using the profile for the prescriber, a transaction record on the computer host for a medical transaction associated with the pharmaceutical prescription.

\* \* \* \* \*